United States Patent [19]

Cox

[11] Patent Number: 4,959,052

[45] Date of Patent: Sep. 25, 1990

[54] APPLICATOR FOR DISPENSING ACTIVE SUBSTANCES

[75] Inventor: Kirsten Cox, Brüggen, Fed. Rep. of Germany

[73] Assignee: Georg Wiegner, Viersen II, Fed. Rep. of Germany

[21] Appl. No.: 342,645

[22] Filed: Apr. 24, 1989

Related U.S. Application Data

[63] Continuation of Ser. No. 3,120, Jan. 14, 1987, abandoned.

[30] Foreign Application Priority Data

Jan. 22, 1986 [DE] Fed. Rep. of Germany ....... 3601787

[51] Int. Cl.$^5$ .......................... A61J 7/00; A61G 17/02
[52] U.S. Cl. ........................................ 604/77; 433/80; 433/218; 604/891.1
[58] Field of Search ................... 604/77, 93, 57, 891.1; 128/136; 424/422–426, 434, 435; 433/80, 81, 183, 189, 201.1, 204, 205, 218, 219, 220, 224, 229

[56] References Cited

U.S. PATENT DOCUMENTS

| | | | |
|---|---|---|---|
| 589,712 | 9/1897 | Fouquier | 604/93 |
| 876,043 | 1/1908 | Davis | 433/220 |
| 1,335,413 | 3/1920 | Abbott | 433/224 |
| 1,721,334 | 7/1929 | Dillman | 604/77 |
| 2,974,567 | 8/1976 | Ridgeway | 433/218 |
| 3,079,690 | 3/1963 | Lödige | 433/81 |
| 3,962,787 | 6/1976 | Corbett | 433/220 |
| 4,252,525 | 2/1981 | Child | 433/201.1 |
| 4,398,887 | 8/1983 | Balde et al. | 433/218 |
| 4,504,230 | 3/1985 | Patch | 433/219 |
| 4,671,768 | 6/1987 | Ton | 433/80 |

Primary Examiner—C. Fred Rosenbaum
Assistant Examiner—Sharon Rose
Attorney, Agent, or Firm—Felfe & Lynch

[57] ABSTRACT

Disclosed is an oral applicator for the application of an active substance in the form of a hollow structure corresponding substantially in shape and dimensions to an external form of a crown of one or more natural teeth and adapted to contain the active substance, the hollow structure having one or more passage openings for the controlled release of certain amounts of the active substance, the passage openings being a buccal and/or palatal or lingual portion for the passage of saliva and of the active substance dissolved therein.

24 Claims, 16 Drawing Sheets

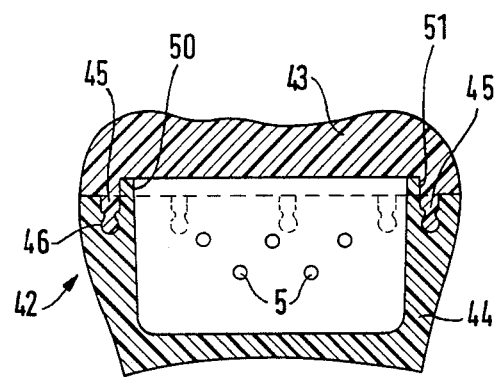
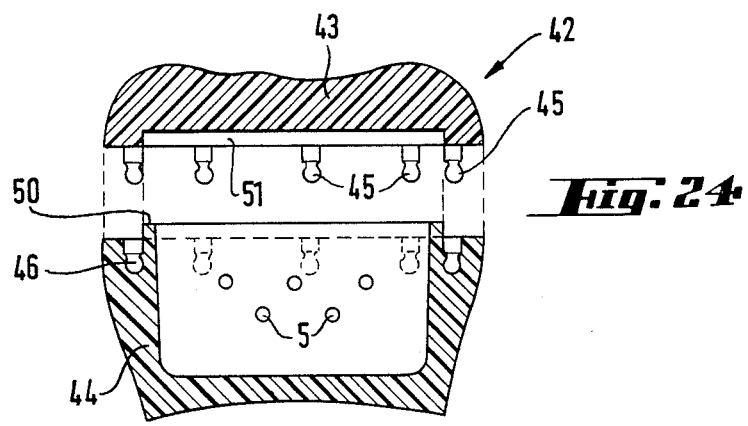

APPLICATOR FOR DISPENSING ACTIVE SUBSTANCES

This application is a continuation of application Ser. No. 003,120, filed Jan. 14, 1987, now abandoned.

BACKGROUND OF THE INVENTION

The invention is in an applicator for dispensing active substances such as medicaments, antibiotics, nutrients, oral care agents, and the like, in the area of the mouth, and artifacts designed for such dispensation.

It is desirable for a number of active substances that they be present in the body in a certain dosage over an extended period of time to maintain a very uniform level of the substances in the organism. Typical examples of such active substances are antibiotics, heart glycosides, pain-killing agents and hormones. Typically, in the early stage of the administration of penicillin, the antibiotic must be administered to the patient within the brief period of 1 to 2 hours, and over night as well to maintain an effective level of the substance in the organism. Likewise, it is desirable to replace or remove the exhausted and worn-out active agents.

Numerous approaches have been proposed and attempted to maintain a very uniform administration of active substances. One approach has been to provide the medicaments with a covering which will dissolve gradually in the stomach or intestinal tract. Other attempts have been based on slowing the breakdown of an active substance in the human or animal body by chemical change and thus achieving a long-sustained and uniform level of the substance. Drip infusion, subcutaneous application, or administration in the form of lozenges and sublingual tablets have also been proposed and/or attempted.

The prior proposed and/or attempted techniques have either been unsatisfactory, as in the case with lozenges and sublingual tablets, or are complicated, inconvenient or have a limited use, i.e., can be used only in stationary treatment. This applies, for example, to subcutaneous use and drip infusion.

DE-OS 32 10 242 discloses a technique based on inserting into the organism's jawbone a tooth implant in which openings are made through which the medicaments are fed directly into the blood stream. The openings can be controlled, thus affecting the rate of dispensation of the medicament. The implant, and especially the valve provided in it for filling with the medicament by means of a syringe, is protected by a releasable protective means. This proposal has found no acceptance in practice and has been relegated to "paper art", mainly because the placement of such an implant requires considerable surgical intervention in the jaw, which a patient accepts only unwillingly, and the surgery can be properly performed by only a limited number of dentists. Due to its complexity, the procedure requires great skill, special tools, and is very costly.

Moreover, such a tooth implant is a foreign body whose presence creates problems, and which often loosens again after a certain amount of time. In the special case involved herein, it also happens that the bone, which defends itself actively against foreign bodies by the formation of new bone substance, may easily block the dispensation opening with new bone substance and thus interfere with the reliable dispensation of medicaments to the organism. Moreover the applicator, in the form of a tooth implant, is limited in its application to the few medicaments which pass directly into the blood and must be sufficiently compatible with bone. This technique does not permit the controlled administration of active substances intended to reach the oral and pharyngeal cavity, such as oral medications or medicaments which are to be absorbed through the mucous membranes, or those which are intended for the treatment of diseases of the oral and pharyngeal cavities.

It is thus an object of the invention to provide an applicator and technique useful in the previously known forms of administration a totally new form of administration which is convenient and reliable in application and which makes it possible, without surgical intervention, to deliver active substances to the organism in uniform dosage over an extended period of time. The previous known form of administration include peroral administration of tablets, drops or capsules, rectal administration in the form of suppositories and capsules, injection and infusion of fluids, administration in the form of aerosols through the lungs, administration through the skin in the form of soaps, pastes or lotions or subcutaneous administration by implantation under the skin, or administration directly into the blood through tooth implants.

SUMMARY OF THE INVENTION

This object and others are obtained by the present invention which is in an applicator for the administration of active substances, such as medicaments, antibiotics, nutrients, mouth care agents and the like, in the area of the mouth, in the form of a hollow structure into which the active substance can be placed and which has openings for the controlled feeding of specific amounts of active substance. The hollow structure largely corresponds in form and dimensions to the external form of the crown of one or more natural teeth and has on the buccal and/or palatal or lingual side at least one opening for the passage of saliva and of the active substances dissolved therein into the oral cavity. Such an opening can be various in nature. In the simplest and preferred form it is simply one or more round holes. However, they can also be in the form of slits, especially when they are advantageously closable by a sliding valve and thus are adjustable to different sizes of opening.

A special advantage of the applicator according to the invention is that it can dispense active substances in the oral and pharyngeal cavity, and that, by means of the number, size or shape of the passage openings, the flow of saliva available for the dissolution and emission of the active substances into the oral and pharyngeal cavity can be controlled. Another special advantage is that the hollow structure itself is simply installed in the mouth, and that the patient can place the active substance in this hollow structure only once a day, e.g., just after brushing the teeth, or only once a week, for the gradual dispensing to the organism. The hollow structure is preferably applied in the oral cavity because active substances are absorbed preferentially through the mucous membranes, or ought to be made available to them, as is the case with oral care substances or medicaments for the neck and throat region. Another advantage lies in the fact that, aside from the single installation of the hollow structure in a manner to be described later on, no other intervention is necessary, and the hollow structure can be situated at points which in most people are unused and available.

In the preferred embodiment of the invention the hollow structure is situated in a gap left between teeth, as is the case, unfortunately, in many people since their earliest youth. Especially advantageous is a hollow structure which can be contained in a hole drilled in a defective tooth, so that the unpleasantness of the dental treatment can be compensated by the positive achievement of having for the rest of one's life a place for the deposit of medication. The hollow structure can be a component of a partial or full dental prosthesis or bridge in those patients so fitted.

When the hollow structure is a component of a bridge the applicator is especially simple to configure and handle if the always necessary opening, or possibility of an opening, for the placement of the active substance is in the form of a hole or slit in at least one lateral wall and the closing of the opening is accomplished in a simple manner in the anchoring of the bridge, in that the opening is closed by one of the two anchoring elements. The advantage of this embodiment lies in the fact that no additional mechanical means, such as hinges, are necessary for opening and closing.

Another advantageous embodiment of the invention consists in a hollow structure as an overlay on the stump of a tooth drilled out to a level close to the pulp. In this manner the new application method is available to persons who have no gaps in their teeth and who do not wear partial or full prosthesis.

In a healthy tooth which has been cut away with a normal tool to a point close to the pulp to utilize the invention, the applicator is preferably in the form of a double crown. Preferably the double crown consists of an inner crown and an outer crown, the inner crown being fastened on the tooth stump and the outer crown seated on the inner crown. A chamber containing the active substance is defined, by or formed between, the inner crown and outer crown. One can gain access to the chamber in different ways. One simple and preferred method consists in lifting off the outer crown, applying the active substance preparation to the inner crown, and then replacing the outer crown. In such an applicator the tooth is preferably cut away such that the top surface of the tooth stump is concave and the active substance preparation is thus held fast in the likewise concave inner crown and cannot roll away.

Another avenue of access to the chamber and introduction of the active substance preparation is for the outer crown to consist of an outer wall and a bite surface part, the latter matching the bite surface of the original tooth and the bite surface part being joined by a hinge to the outer wall.

In another advantageous embodiment the applicator is constructed as a slide or drawer, open on one side, but otherwise closed, which can be slid upwardly and downwardly or inwardly and outwardly to a stop, so that the active substance can be placed in it while it is in the open position.

In the case of a devitalized tooth, a modified form of applicator is advantageous. The inner crown is in this case in the form of an open cup which is fastened in the roots of the tooth by means of screws entering the root canals. An outer crown is superimposed on this cup-like inner crown. In this case both the inner crown and the outer crown have passage openings, those of the inner crown being larger than those of the outer crown. By turning the two crowns the size if the passage openings can be adjusted to control the emission of the active substance preparation.

In another advantageous embodiment of the invention, the applicator is in the form of a hollow artificial tooth of a two-part construction and consists of a bite surface part and a base part, the base part accommodating the active substance preparation and having openings for saliva passage.

In addition to the control of the amount of active substance released to the organism by means of the size, shape and number of the passage openings, additional measures can be taken to extend the time of action. One advantageous method consists in using a chemical reaction to render the active substances located in the hollow structure controlledly resistant to the saliva serving as the transport medium. An additional preferred method is to mix inert substances with the active substance in the hollow structure for the purpose of delaying the access of the saliva. It has also been found desirable to provide the active substances in the hollow structure with a covering that makes them controlledly resistant to the attack of the saliva.

The various features of novelty which characterize the invention are pointed out with particularity in the claims annexed to and forming a part of this specification. For a better understanding of the invention, its operating advantages and specific objects obtained by its use, reference should be had to the accompanying drawings and descriptive matter in which there is illustrated and described a preferred embodiment of the invention.

BRIEF DESCRIPTION OF THE DRAWINGS

FIG. 23 is a side view of a cross section of a variation of the structure of FIG. 20; and FIG. 24 is an exploded view of the tooth of FIG. 23.

DESCRIPTION OF PREFERRED EMBODIMENTS

Figure 4:
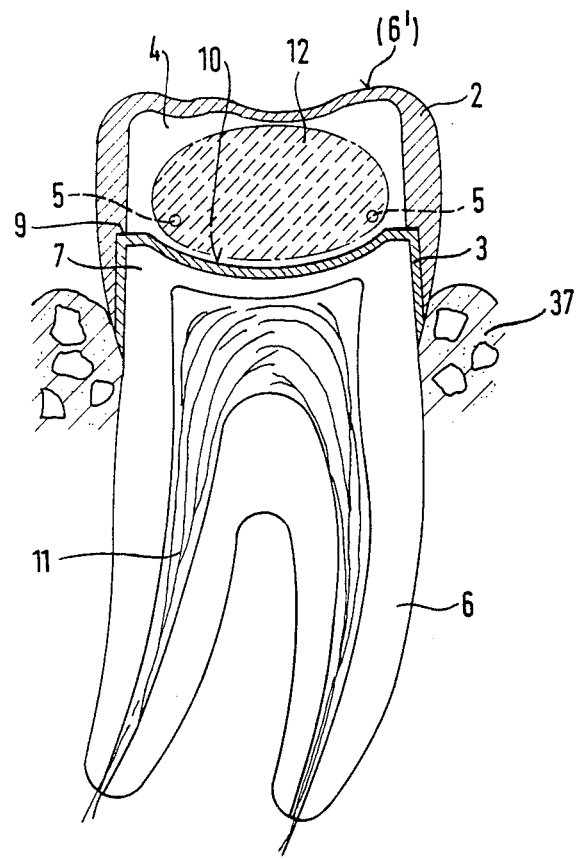
FIG. 4 shows another embodiment of the invention in the form of a double crown arrangement.
Figure 5:
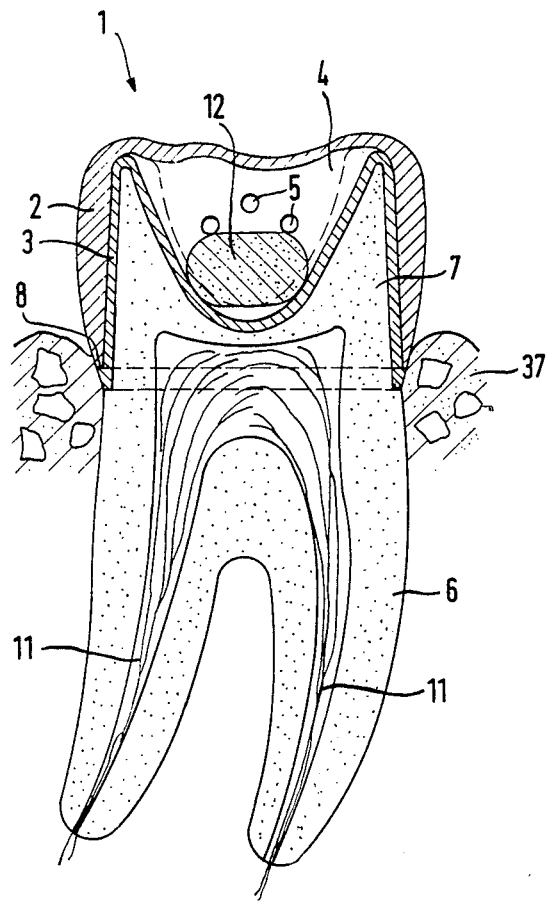
FIG. 5 shows a variant of the double crown arrangement of FIG. 4.
Figure 6:
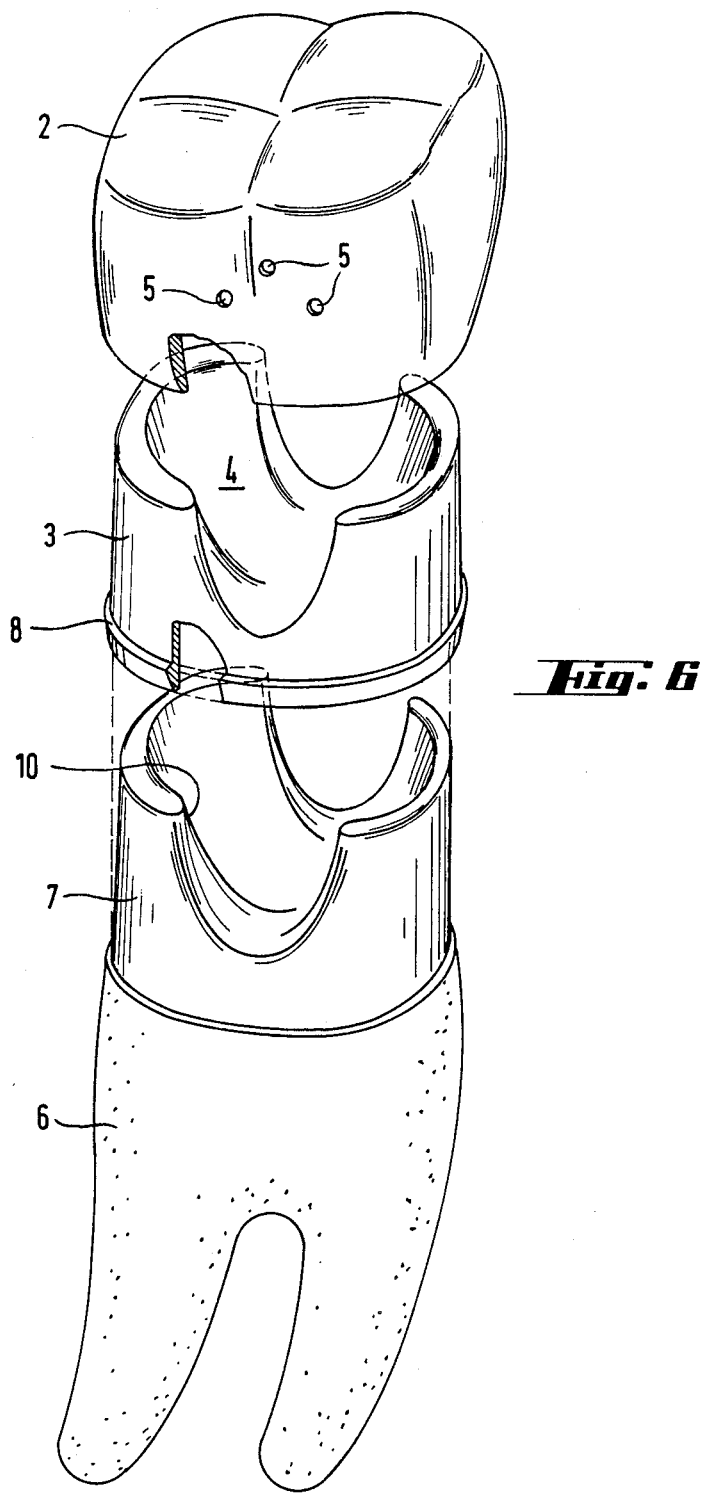
FIG. 6 is an exploded full view of the construction of FIG. 5.

FIGS. 4 to 6 show a preferred embodiment of an applicator of the invention in the form of a double crown 1 (FIG. 5). FIGS. 4 and 5 are side views in cross section. FIG. 6 is an exploded view corresponding to a full view of FIG. 5.

As shown in FIGS. 4 and 5, a vital tooth 6 has been cut away to a level close to pulp 11 with a standard drill developed for such applications. An inner crown 3 is cemented onto stump 7 of the tooth. The upper surface or table 10 of the inner crown 3 is of a concave shape as is that of stump 7. An outer crown 2 is hollow on the interior and provided with one or more openings 5 for the passage of saliva and the dissolved active substance. Outer crown 2 is superimposed on the inner crown 3. The inner crown 3 and the outer crown 2, which at the top corresponds to the original bite surface of the natural tooth 6', define and/or enclose a chamber 4 to accommodate the active substance preparation 12 and together form the applicator.

As shown in FIG. 4, the outer crown 2 has, on its inner lateral circumferential surface, a step 9, so that the outer crown 2 is held not just at the sides on the inner crown 3 but also is fixed vertically in position on the inner crown 3. This construction also permits increasing the wall thickness of the outer crown 2 without altering the anatomy of the oral cavity.

As shown in FIGS. 5 and 6, an abutment for the outer crown 2 is in the form of a step 8 on the inner crown 3. This embodiment has the advantage that the outer crown 2 can be made with a relatively thin wall and can be kept light in weight. In this embodiment the tooth stump 7 is cut such that the shaft of the tooth has been kept comparatively high alongside the adjacent teeth, so that the inner crown 3 mounted thereon will serve in this area as a support for the outer crown. On the inside and outside, i.e., on the buccal side and on the palatal or lingual side, as the case may be, the tooth stump 7 is cut away to a greater degree. By this different height of the outer circumference of the tooth stump 7, on the one hand a more secure friction fit of the outer crown 2 is achieved, and likewise a secure containment of the active substance preparation 12 in the chamber 4, and on the other hand, the openings 5 have a free connection to the active substance chamber 4 on the inside and outside, i.e., on the buccal side and on the palatal or lingual side, so that the passage of saliva and dispensing of the active substances by means of the saliva are assured.

Figure 1:
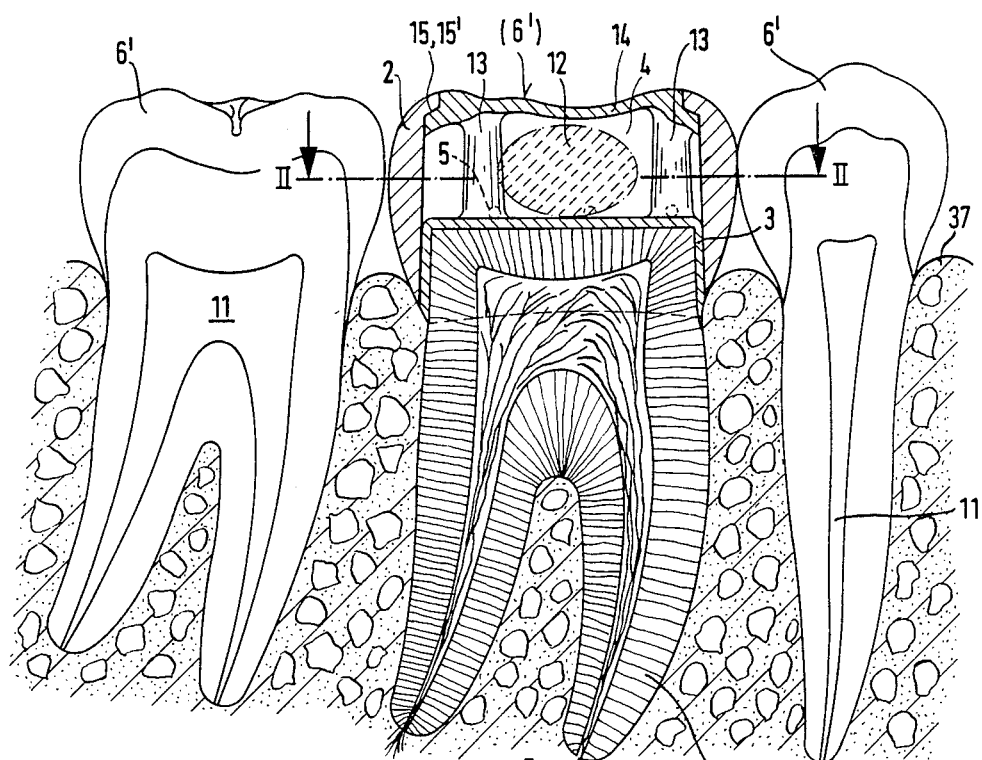
FIG. 1 shows a longitudinal cross section of a cut natural tooth adapted with a form of the invention between two uncut teeth.
Figure 2:
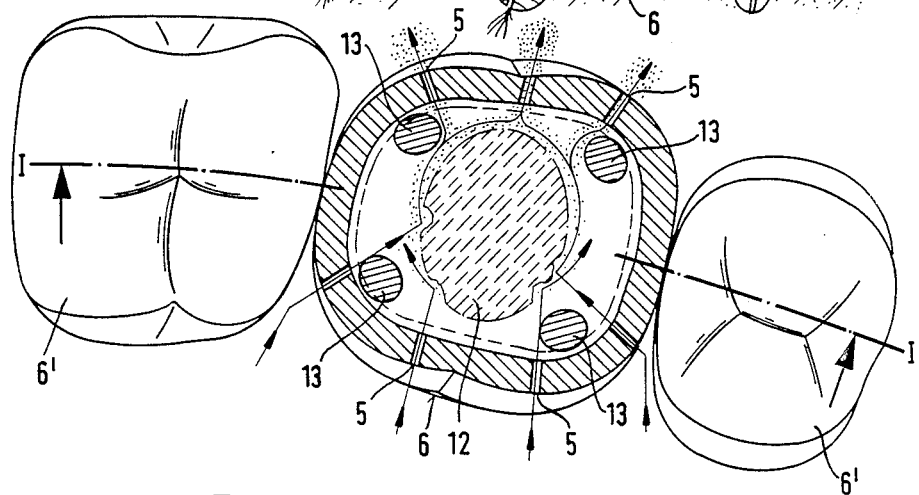
FIG. 2 is a plan view of along view line II—II of FIG. 1.
Figure 3:
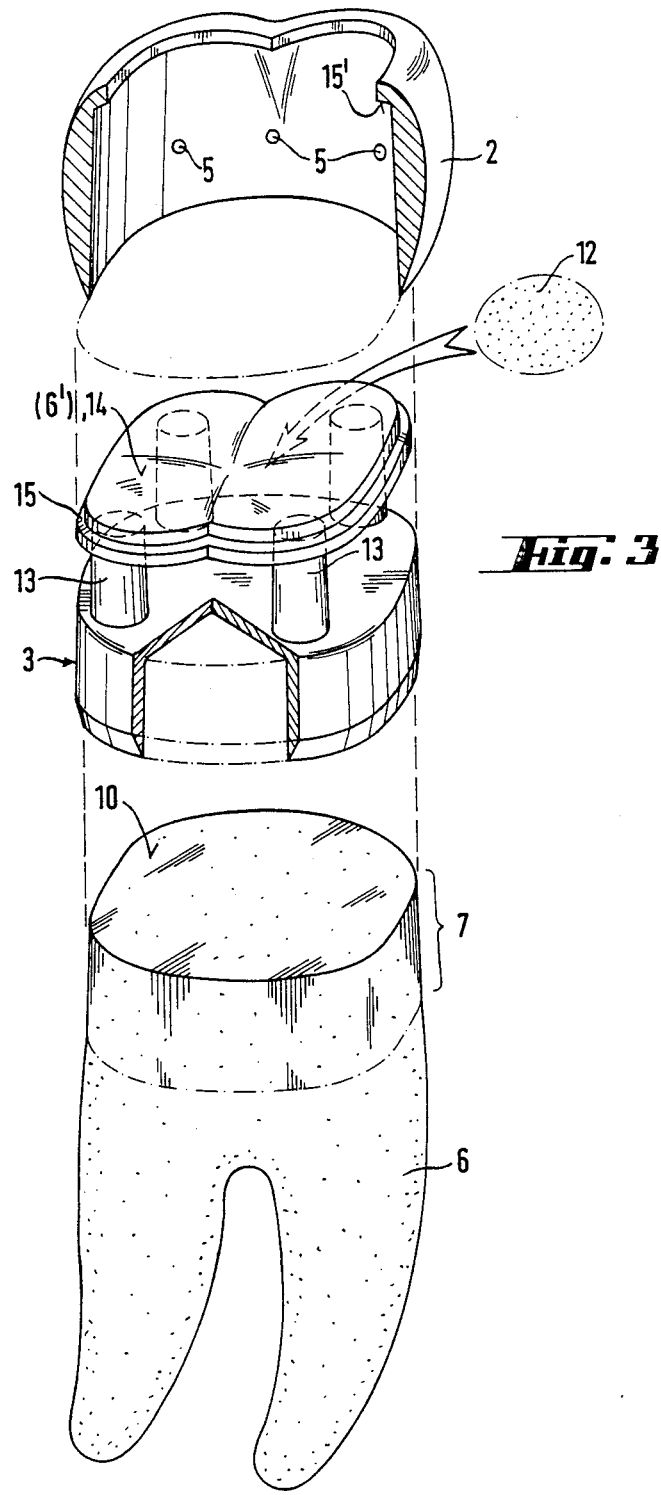
FIG. 3 is an exploded perspective view of the applicator of FIGS. 1 and 2.

The embodiment according to FIGS. 1 to 3 differs from the one in FIGS. 4 to 6 in that the inner crown 3 is of a stool-like configuration and is joined in one piece by legs 13 to the bite surface part 14, the surface of the bite surface part 14 corresponding to the bite surface of the original natural tooth 6'. The outer crown 2, which is open in this case, is mantle-like and slightly constricted at the top of 15', so that, after the insertion of the active substance preparation 12, in the form of a pill, for example, between the legs 13, it is placed over the bite surface part 14 and the inner crown 3, the constricted part 15' of the outer crown 2 coming to rest on the step 15 on the bite surface part 14. FIG. 1 shows in longitudinal cross section a natural tooth 6 that has been cut accordingly, between two teeth 6' that have not been cut, and the embedding of the teeth 6 and 6' in the jawbone 37.

FIG. 2 shows the same teeth 6, 6', in a cross-sectional top view in which the arrows indicate the attack of the saliva through the passage openings 5 on the active substance preparation 12, whose dissolution and emergence are indicated by arrows drawn through the openings 5. FIG. 3 is the representation of the same applicator in an exploded perspective view.

Figure 7:
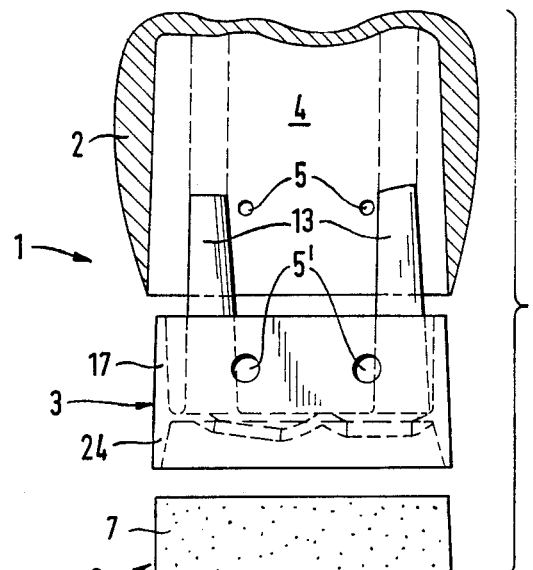
FIG. 7 is a partially exploded view of FIG. 8.
Figure 8:
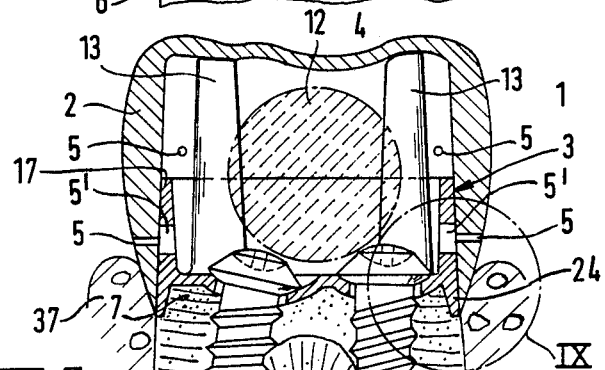
FIG. 8 is a front section view of an alternate embodiment of the invention.
Figure 9:
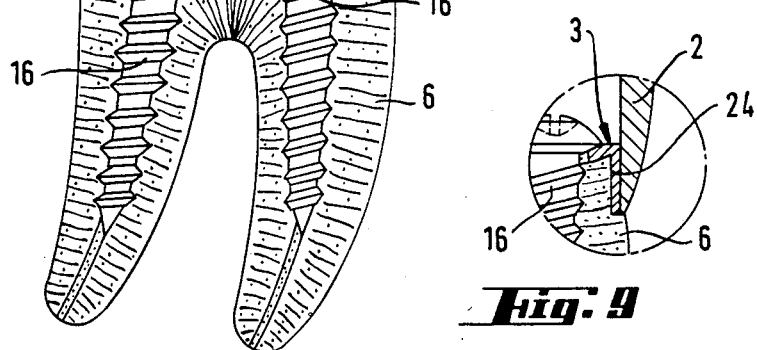
FIG. 9 shows a variant of the embodiment of the invention as shown in FIGS. 7 and 8.

FIGS. 7 to 9 show an applicator, again in the form of a double crown on a devitalized tooth 6 from which the tooth nerve has been removed. The tooth 6 is in this case cut away down to the top of the pulp cavity. The inner crown 3 is in this case in the form of a cup 17 open at the top, which is fastened into the roots of the tooth 6 by means of screws 16 driven into the root canals. At the bottom, the side wall of the inner crown 3 is slightly lengthened and forms a crown 24 which protects the tooth stump 7. Here again the inner crown 3 serves as a mounting for the outer crown 2. In this example, in addition to the passage openings 5 in the outer crown 2, larger passage openings 5' are located in the cup 17. The cup 17 also has posts 13 on which the outer crown 2 rests, so that the posts 13 serve as an abutment for the outer crown 2. FIG. 7 is a partially exploded view of FIG. 8.

FIG. 9 shows a variant of the embodiment of FIGS. 7 and 8, in which the cup 17 is omitted and only the crown 24 serves as a seat for the outer crown 2, so that a configuration results which is similar to that of FIGS. 1 to 6.

FIGS. 10 to 13 show an applicator which utilizes a gap between teeth and is a component of a bridge 18 which is anchored to the teeth A and C (FIGS. 12 and 13) and spans the gap left by the former tooth B. A component of this bridge 18 is bridge member 19 serving as an applicator for active substances, which has on the sides a slide 20 adjacent the neighboring teeth A and C, so that the bridge member 19 can be pulled upwardly by a ball knob 25 or a notch 26 (FIGS. 10 and 11) provided as holds, up to an abutment 21, releasing opening 27 through which the active substance preparation 12 can be inserted. For this purpose bridge member 19 has on one side a spring 22 which slides in a groove 23.

Figure 10:
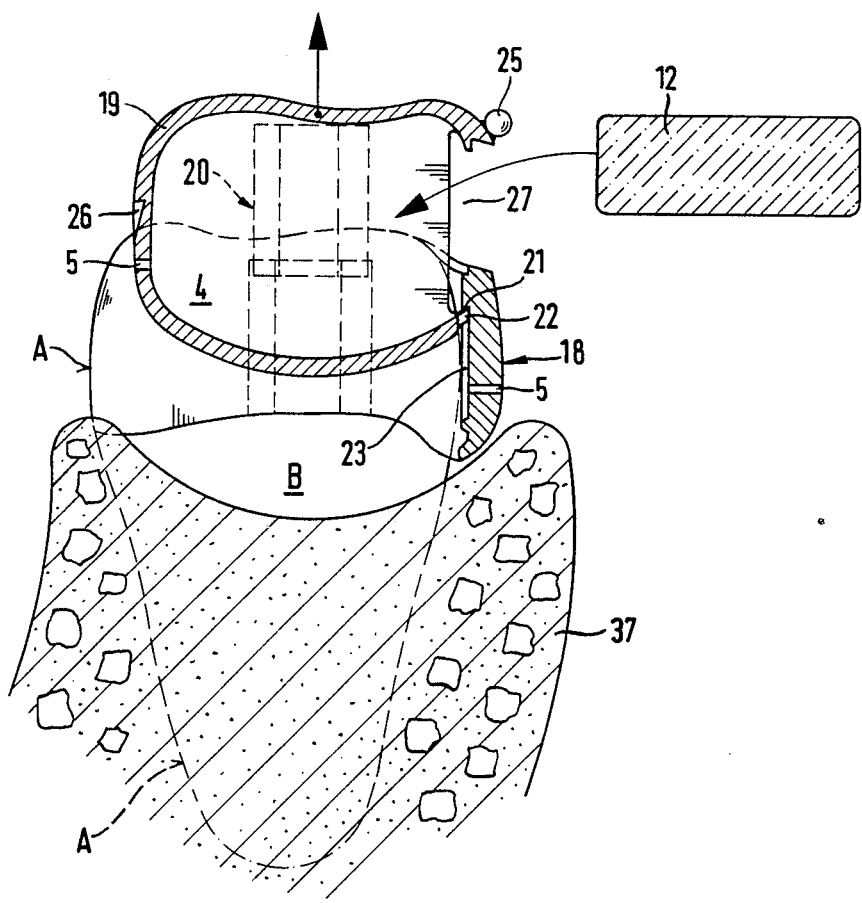
FIG. 10 shows a bridge member in the open state.
Figure 11:
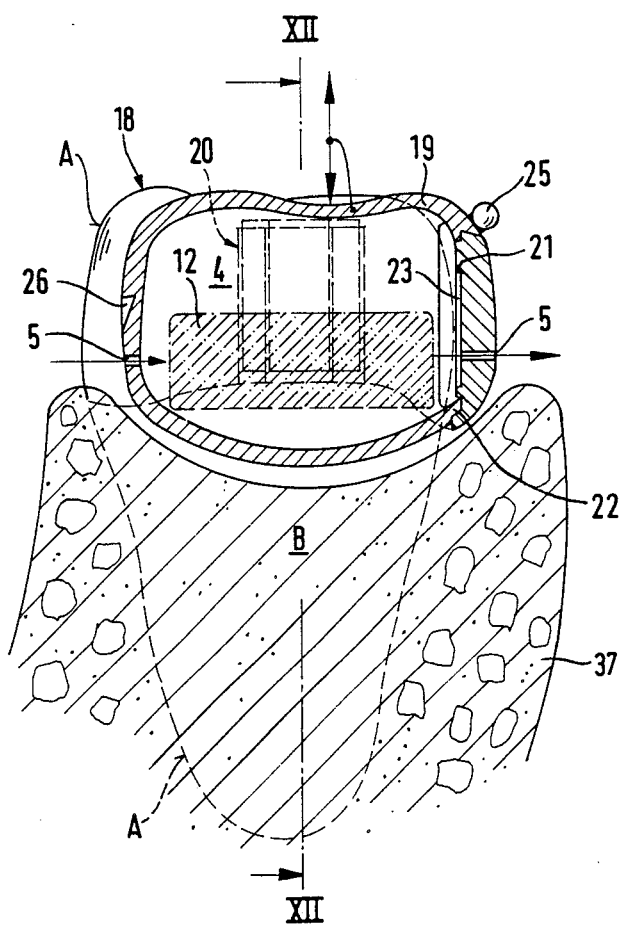
FIG. 11 is similar to FIG. 10, but the bridge member is in a closed state.
Figure 12:
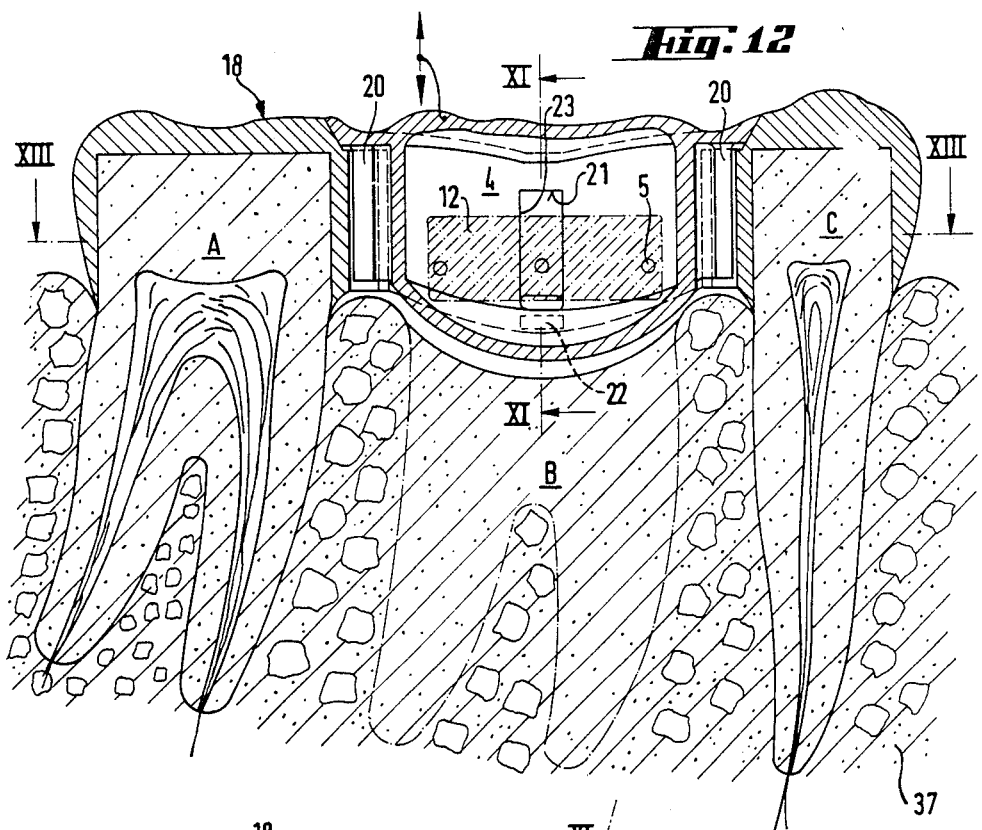
FIG. 12 shows the incorporation of a bridge member 19 into bridge 18 along view line XII—XII of FIG. 11.
Figure 13:
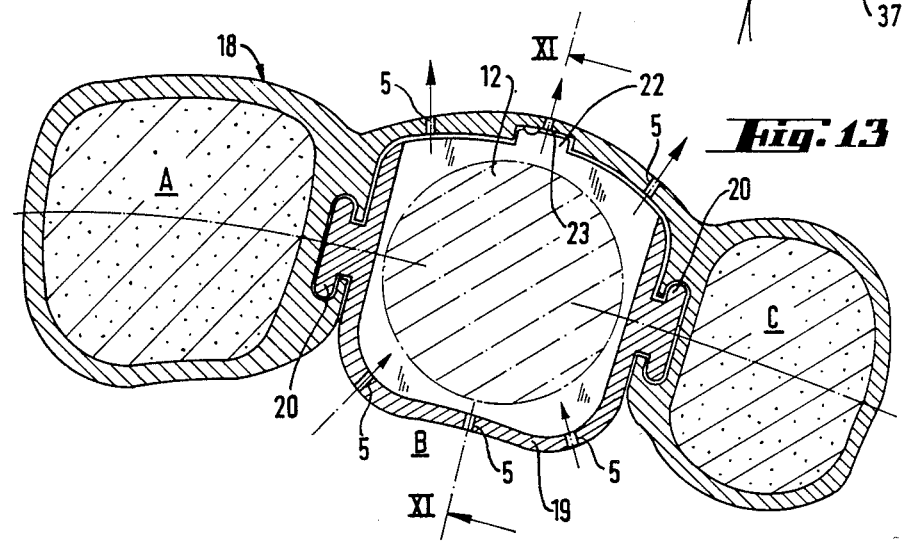
FIG. 13 is a plan view along view line XIII—XIII of FIG. 12.

FIG. 10 shows the bridge member 19 in the open state, in a cross-sectional side view. FIG. 11 shows the bridge member in the closed state. FIG. 12 shows the incorporation of the bridge member 19 into the bridge 18 and its anchorage on the teeth A and C, in a cross-sectional side view, and FIG. 13 the top view, also in cross section.

Figure 14:
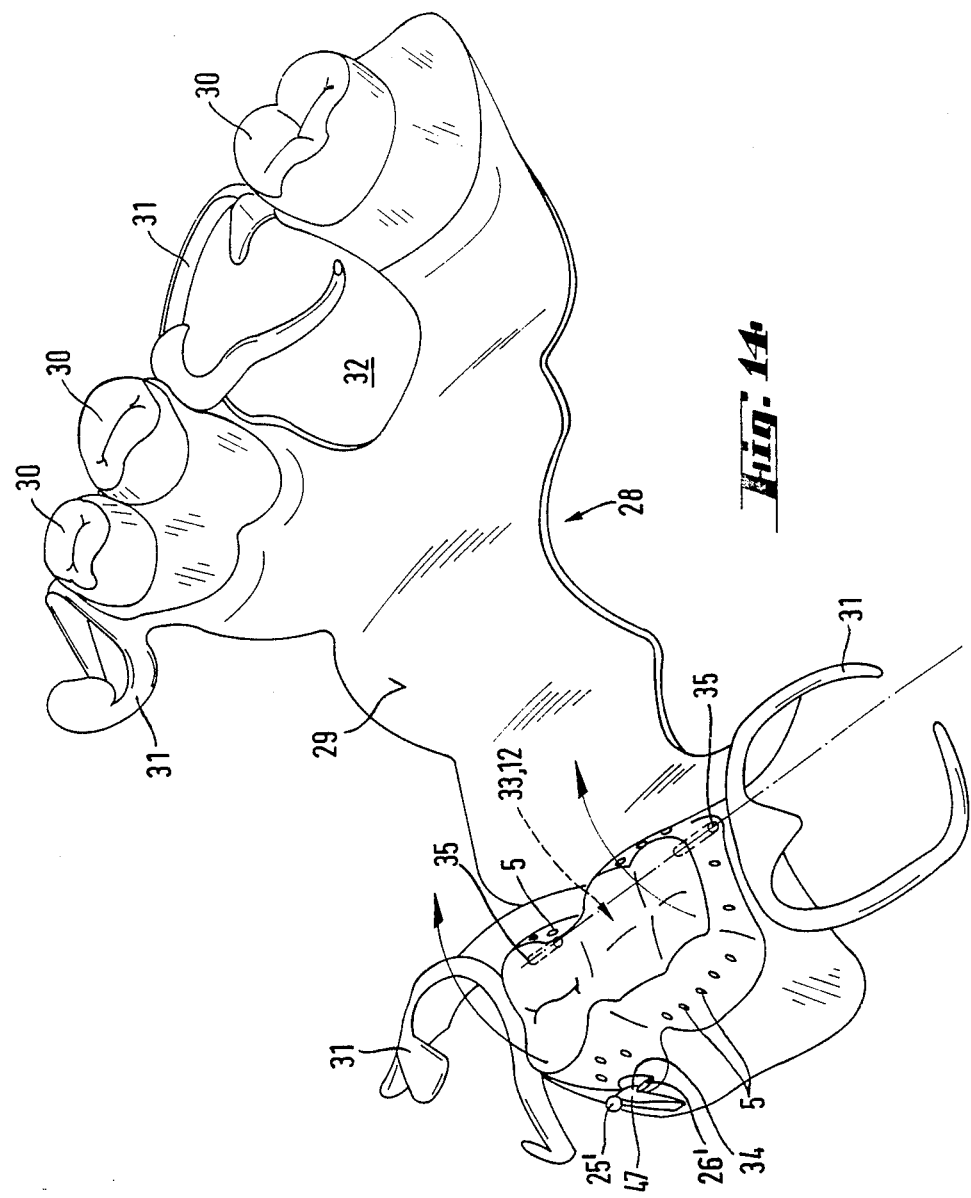
FIG. 14 shows an applicator as a component of a partial prosthesis.

FIG. 14 shows an applicator as a component of a partial prosthesis 28 which consists of a palatal plate 29 or arch to which artificial teeth 30 are fastened on both sides. The partial prosthesis 28 is attached by means of clasps 31 to teeth still present, which are not shown. The right portion of the partial prosthesis 28 has an opening 32 to accommodate a natural tooth that is still present. The two artificial teeth 30 on the left side of the partial prosthesis 28 are in the form of double chamber 33, so that either larger amounts of active substance preparation, or different preparations 12, can be contained therein. In this embodiment the applicator can be opened on the hinge 35 for the insertion of the active substance preparation 12, a ball 25' serving as the knob of a catch lever 47, and the lockup being accomplished by means of the catch 34 snapping into the notch 26'.

Figure 15:
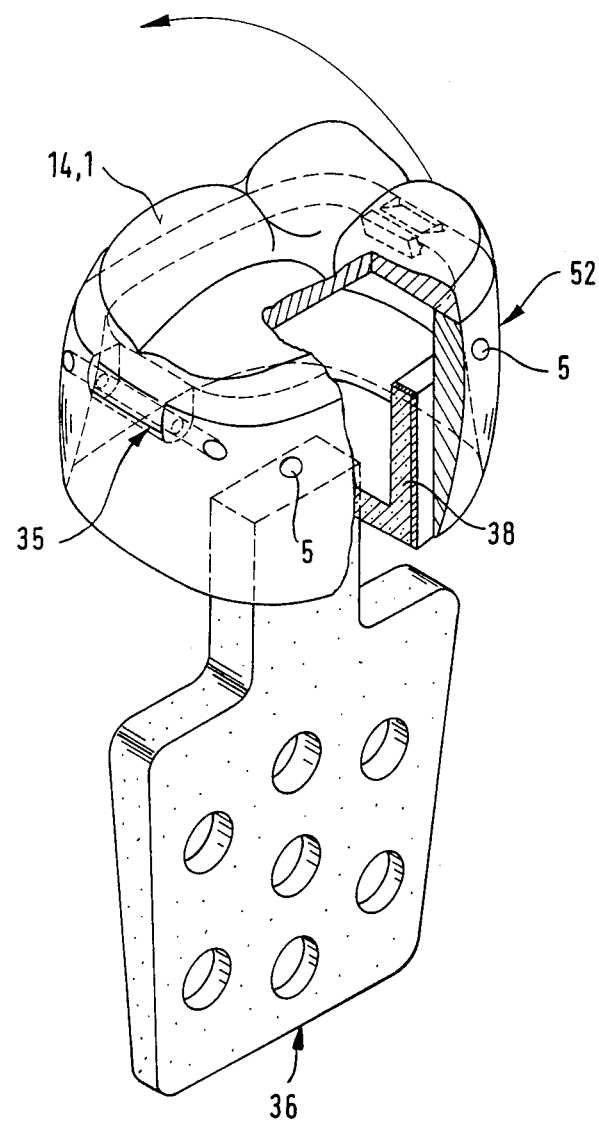
FIG. 15 shows a perspective view in partial cross section of a tooth implant.
Figure 16:
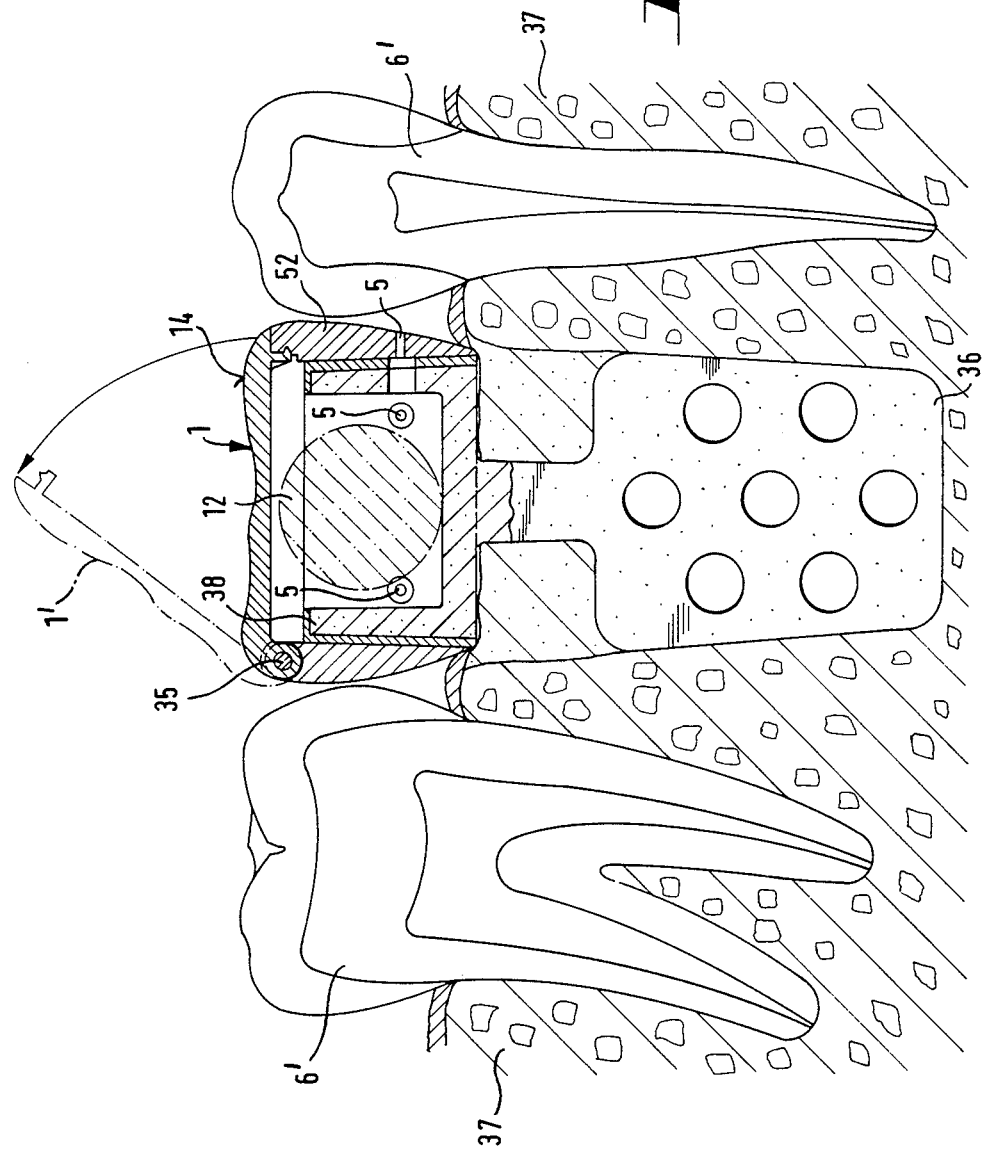
FIG. 16 shows a side view in cross sectional of the implant between two existing teeth.

FIGS. 15 and 16 show an applicator in conjunction with a tooth implant 36 in flat plate form, which in its upper part projecting from the jawbone 37 is in the form of a cage 38 on which a hollow crown 52 is mounted. The bite surface part 14 of the crown can open on a hinge 35. FIG. 15 shows a perspective view, partially in cross section, of the tooth implant 36 by itself, and FIG. 16 shows it in a cross-sectional side view, embedded between two existing teeth 6'.

Figure 17:
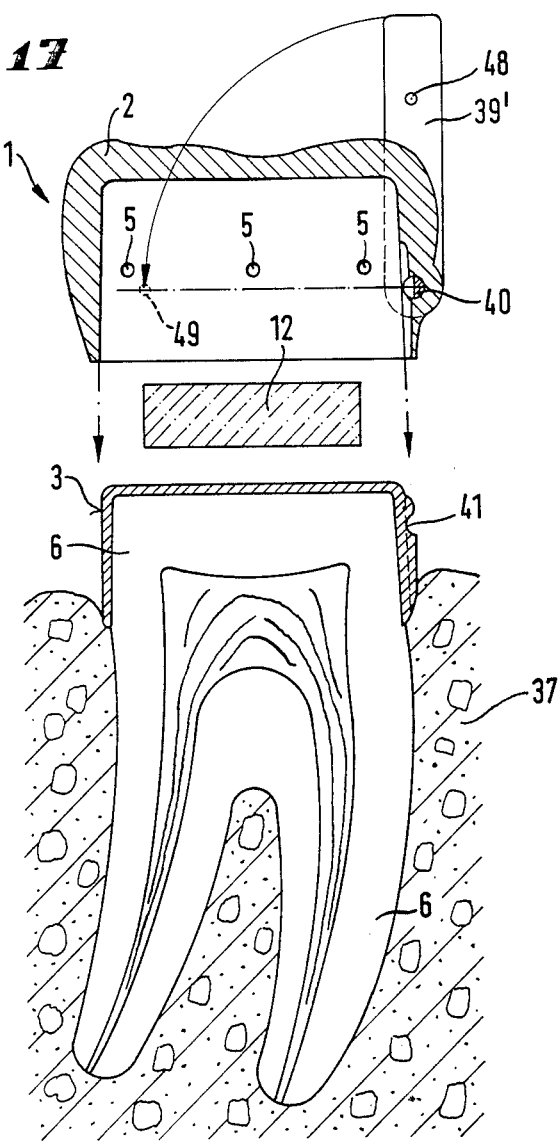
FIG. 17 shows another applicator of the invention in an exploded view.
Figure 18:
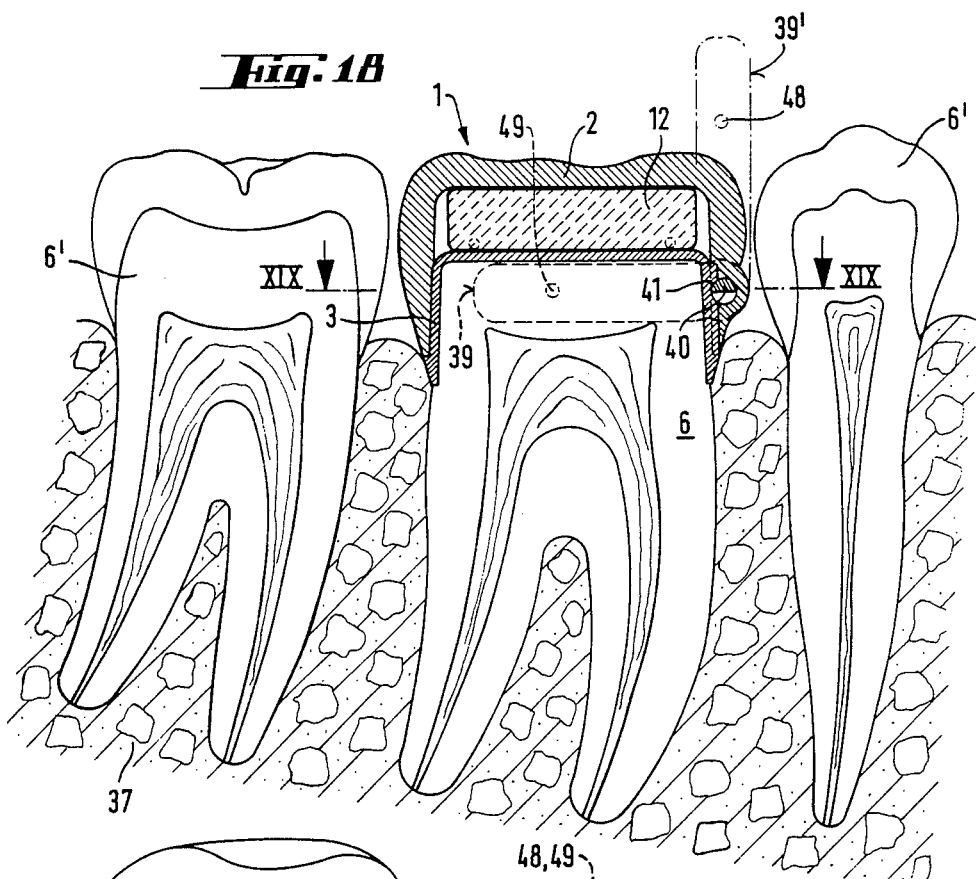
FIG. 18 is a cross section side view with adjacent teeth.
Figure 19:
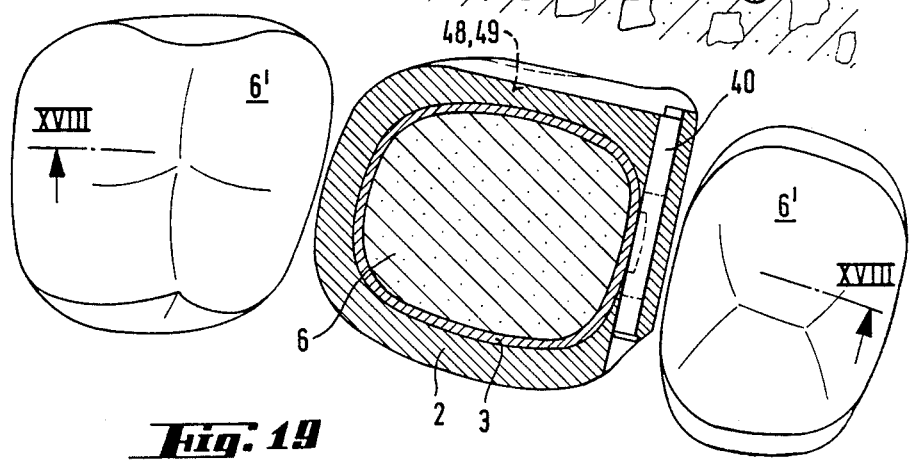
FIG. 19 is a view along view line XIX—XIX of FIG. 18.

FIGS. 17 to 19 show an applicator similar to FIGS. 4 to 6, in the form of a double crown 1 with an outer crown 2 and inner crown 3 on a truncated tooth 6. In this embodiment the outer crown 2 is joined to the inner crown 3 by the lever 39 engaging it externally on one side. When the lever 39 is raised, as indicated at 39', the double crown 1 can be lifted up and away. After the active substance preparation 12 has been applied to the inner crown 3, the outer crown 2 is returned to its place, the lever 39 is pressed down, and the outer crown 2 is thus locked on the inner crown 3. The locking hinge pin 40 is then engaged in the detent groove 41 and prevents unintentional release of the outer crown 2. The lever 39 is provided with a detent 48 thereon. The outer crown 2 has an indentation 49 (FIG. 19) which prevents unintentional release of the lever 39. FIG. 17 is an exploded view of this embodiment, FIG. 18 is a side view in cross section in the closed state together with adjacent teeth 6', and FIG. 19 is a top view, partially in cross section.

FIGS. 20 to 24 show an applicator in the form of a hollow plastic tooth 42 composed of a plastic bite surface part 43 and a base part 44 for accommodating the active substance preparation 12. The plastic bite surface part 43 and base part 44 are connected to one another by pins 45 which engage sockets 46. In the embodiment in FIGS. 23 and 24, the base part 44 has an additional rim 50 which engages a corresponding cylindrical recess 51 in the plastic bite surface part 43, so that the plastic bite surface part 43 is provided with additional lateral stability.

Figure 20:
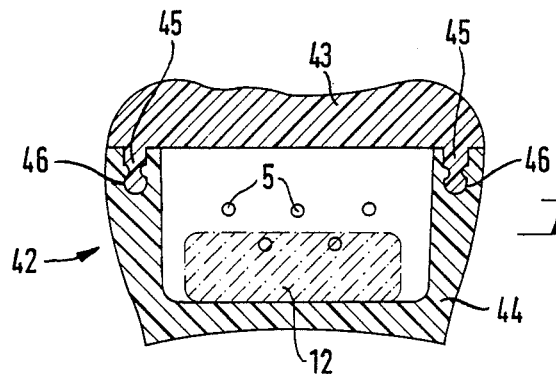
FIG. 20 shows a side view in cross section of the applicator of the invention in the form of a hollow plastic tooth.
Figure 21:
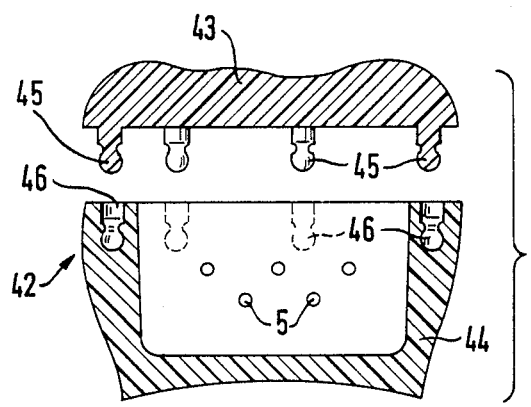
FIG. 21 is an exploded view of the tooth of FIG. 20.
Figure 22:
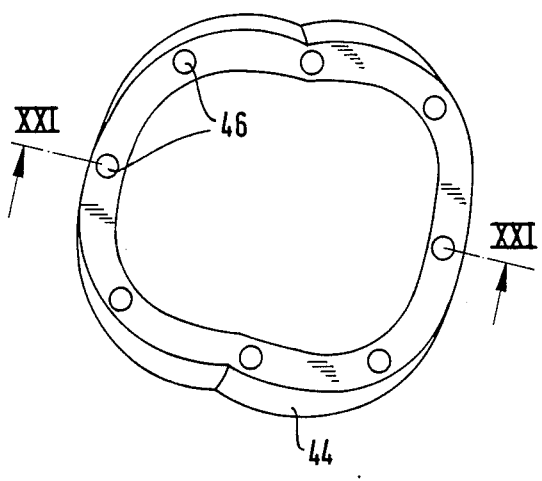
FIG. 22 is a plan view of the base of the tooth of FIG. 21.

FIGS. 20 and 23 are side views in cross section, FIGS. 21 and 24 are corresponding exploded view, and FIG. 22 a top view of the base part 44.

The materials of the applicator can be any materials known and established in the art of dentistry, such as gold, noble metal reduced, base metals, and physiologically acceptable plastics.

It will be understood that the specification and examples are illustrative but not limitative of the present invention and that other embodiments within the spirit and scope of the invention will suggest themselves to those skilled in the art.

I claim:

1. An oral applicator for the application of an active substance to a user having an oral cavity comprising: a hollow structure corresponding substantially in shape and dimensions to an external form of a double crown of one or more natural teeth and adapted to contain the active substance, wherein said double crown is comprised of an inner crown adapted for engagement with a cut-away tooth stump and of an outer crown placed thereon, said hollow structure having one or more passage openings adapted for the controlled release of certain amounts of the active substance to the oral cavity, the one or more passage openings being at least one of a buccal, palatal or lingual portion for the passage of saliva and of the active substance dissolved therein.

2. The hollow structure of claim 1 in the form of an insert to be set in as a cap, said insert having means for attaching to a tooth stump cut away almost down to the tooth pulp.

3. The hollow structure of claim 1 wherein the inner crown is a cup open at the top and has at least one passage opening, and the outer crown is rotatable on the inner crown so that various areas of the least one passage opening can be covered by varying the position of the outer crown with respect to the inner crown.

4. The hollow structure of claim 1 wherein the hollow structure is in the form of a slide and in the open position has a freely accessible opening for the introduction of the active substance preparation.

5. The hollow structure of claim 1 wherein the outer crown is fastened on the inner crown for release by a lever.

6. The hollow structure of claim 1 wherein the hollow structure is a plastic tooth which consists of a bite surface part and a base part for receiving the active substance preparation.

7. The hollow structure of claim 1 as the upper component of a tooth implant.

8. The hollow structure of claim 5 wherein the hollow structure is fastened on a tooth implant.

9. The hollow structure of claim 1 wherein the active substance contained in the hollow structure is provided with a coating having controlled resistance to saliva.

10. The hollow structure of claim 1 wherein the active substance contained in the hollow structure is rendered controlledly resistant to saliva by chemical reaction.

11. The hollow structure of claim 10 wherein inert substances are admixed with the active substances to render the active substances controlledly resistant to saliva.

12. A hollow structure for the oral administration of an active substance to a user having an oral cavity with a tooth stump and gum line therein, the hollow structure comprising:
an inner crown with means for setting the inner crown in as a cap on the tooth stump;
an outer crown which has one or more passage openings for the controlled release of certain amounts of the active substance to the mouth of the user, the one or more passage openings being at least one of a buccal, palatal or lingual portion for the passage of saliva and of the active substance dissolved therein above the gum line to the mouth of the user, said inner and outer crown having means to engage one another to form a double crown which corresponds substantially in shape and dimensions to an external form of one or more natural teeth and is adapted to contain the active substance.

13. The hollow structure of claim 12 wherein the outer crown is fastened to the inner crown by clamping the inner face of the side wall of the outer crown to the outer face of the side wall of the inner crown.

14. The hollow structure of claim 12 wherein the inner crown has a top surface which is concave.

15. The hollow structure of claim 12 wherein the inner crown has a height on the inside and outside, i.e., on the buccal side and on the palatal or lingual side which is less than the height along the adjacent teeth.

16. The hollow structure of claim 12 wherein the hollow structure is closed off by a bite surface part.

17. The hollow structure of claim 22 wherein the bite surface part is connected to the hollow structure by a hinge for opening the bite surface part.

18. The hollow structure of claim 12 wherein the outer crown is fastened to the inner crown by a lever.

19. The hollow structure of claim 12 wherein the inner crown has a cup open at the top and has at least one passage opening.

20. The hollow structure of claim 19 wherein the outer crown is rotatable on the inner crown so that various areas of the least one passage opening of the inner crown can be covered by varying the position of the outer crown with respect to the inner crown.

21. The hollow structure of claim 12 wherein the outer crown has an inner lateral circumferential surface on which is formed a step.

22. The hollow structure of claim 12 wherein the inner crown has a step at a lower section thereof.

23. The hollow structure of claim 12 including means for removing and replacing the outer crown.

24. A hollow structure for the oral administration of an active substance to a user having an oral cavity and gum line therein, the hollow structure comprising:
an inner crown including means for said inner crown being a part of a tooth implant;
an outer crown having one or more passage openings for the controlled release of certain amounts of the active substance to the mouth of the user, the one or more passage openings being at lease one of a buccal, palatal or lingual portion for the passage of saliva and of the active substance dissolved therein above the gum line to the mouth of the user, said inner and outer crown adapted to engage one another to form a double crown which corresponds substantially in shape and dimensions to an external form of one or more natural teeth and is adapted to contain the active substance.

* * * * *